US006890483B2

United States Patent
Andreoli et al.

(10) Patent No.: US 6,890,483 B2
(45) Date of Patent: *May 10, 2005

(54) NON-LUMINESCENT SUBSTRATE (75) Inventors: Rita J. Andreoli, Thomaston, CT (US); Richard S. Chesterson, Meriden, CT (US)

(73) Assignee: Cuno Incorporated, Meriden, CT (US)

( * ) Notice: Subject to any disclaimer, the term of this patent is extended or adjusted under 35 U.S.C. 154(b) by 662 days.

This patent is subject to a terminal disclaimer.

(21) Appl. No.: 09/897,333

(22) Filed: Jul. 2, 2001

(65) Prior Publication Data

US 2002/0019481 A1 Feb. 14, 2002

Related U.S. Application Data (60) Provisional application No. 60/216,229, filed on Jul. 5, 2000.

(51) Int. Cl.[7] ............................................... G01N 21/64
(52) U.S. Cl. ........................ 422/55; 422/57; 422/82.08; 422/82.11
(58) Field of Search ................................ 422/82.11, 55, 422/57, 82.08; 356/244; 436/165, 172

(56) References Cited

U.S. PATENT DOCUMENTS

| | | | |
|---|---|---|---|
| 3,876,738 A | 4/1975 | Marinaccio et al. .......... 264/41 |
| 4,473,475 A | 9/1984 | Barnes, Jr. et al. ......... 210/638 |
| 4,645,602 A | 2/1987 | Barnes, Jr. et al. ......... 210/490 |
| 4,837,162 A | 6/1989 | Rothman et al. | |
| 4,921,878 A | 5/1990 | Rothman et al. | |
| 5,006,287 A | 4/1991 | Davis | |
| 5,062,691 A | 11/1991 | Tristani-Kendra et al. | |
| 5,124,128 A | * | 6/1992 | Hildenbrand et al. ......... 422/56 |
| 5,420,047 A | 5/1995 | Brandt et al. | |
| 5,601,997 A | 2/1997 | Tchao ........................... 435/29 |
| 5,688,642 A | 11/1997 | Chrisey et al. ................. 435/6 |
| 5,712,383 A | 1/1998 | Sheridan et al. ........... 536/24.3 |
| 5,858,309 A | 1/1999 | Mathus et al. ............... 422/102 |
| 5,858,804 A | 1/1999 | Zanzucchi et al. ........... 436/536 |
| 5,919,626 A | 7/1999 | Shi et al. ......................... 435/6 |
| 5,976,336 A | 11/1999 | Dubrow et al. .............. 204/453 |
| 6,048,695 A | 4/2000 | Bradley et al. .................. 435/6 |
| 6,056,529 A | 5/2000 | Meyering et al. ............ 425/143 |
| 6,066,446 A | 5/2000 | Mullinax et al. ............... 435/4 |
| 6,087,102 A | 7/2000 | Chenchik et al. ............... 435/6 |
| 6,118,126 A | * | 9/2000 | Zanzucchi ................ 250/458.1 |
| 6,387,631 B1 | 5/2002 | Arnold et al. ................... 435/6 |
| 6,734,012 B2 | * | 5/2004 | Andreoli et al. .......... 435/287.1 |

FOREIGN PATENT DOCUMENTS

| | | |
|---|---|---|
| EP | 0 605 828 A1 | 7/1994 |
| EP | 0 614 987 A | 9/1994 |
| WO | WO 99/40038 | 8/1999 |
| WO | WO 01/61042 A2 | 8/2001 |

OTHER PUBLICATIONS

U.S. Provisional Application No. 60/216, 229 filed Jul. 5, 2000.
ASTM (American Society for Testing and Materials)—DisIgnation: E 1294–89 (Reapproved 1999) Standard Test Method for Pore Size Characteristics of Membrane Filters Using Automated Liquid Porosimeter—This test method uses the automated bubble point method described in ASTM Test Method F316, pp. 1 and 2 of 2 (no month).
International Search Report of counterpart PCT application No. PCT/US01/20979 mailed Nov. 29, 2002.

* cited by examiner

Primary Examiner—Jeffrey R. Snay
(74) Attorney, Agent, or Firm—R. Thomas Payne; John A. Tomich (57) ABSTRACT A substantially non-reflective, low or non-fluorescing substrate comprising a phase-inversion support and a plurality of opaque solids that are substantially chemically non-reactive with the phase inversion support and of a size sufficient to be partially or completely contained within, or intimately bound to, the phase inversion support. Methods of making and using the substantially non-reflective, low or non-fluorescing substrate are also disclosed.

44 Claims, 6 Drawing Sheets

NON-LUMINESCENT SUBSTRATE

RELATED APPLICATIONS

This application is a continuation-in-part of commonly owned U.S. Provisional Patent Application Ser. No. 60/216,229 of Andreoli, filed Jul. 5, 2000, entitled "IMPROVED NON-LUMINESCENT SUBSTRATE," the disclosure of which is herein incorporated by reference to the extent not inconsistent with the present disclosure.

BACKGROUND OF THE DISCLOSURE

The present disclosure relates to an improved fluorescent-quenching substrate comprising a phase inversion support associated with a plurality of opaque solids that are substantially non-reactive chemically with the phase inversion support and that are of a size sufficient to be partially or completely contained within, or irreversibly bound to, the phase inversion support. Such substrate may advantageously be employed in bioaffinity assays, including immunoassays and nucleic acid binding assays, which utilize luminescent tags, such as fluorescent tags. Such substrate further has use as filtration media to efficiently remove organic and/or inorganic material from fluids.

A great variety of assay systems have been developed to detect the presence and concentration of analytes in samples. For example, bioaffinity and enzymatically-activated catalysis reactions are widely used in medicine and science to analyze biological samples to detect and quantitize biological materials of concern. Many of these assay systems depend upon the binding of one chemical entity with the material of concern (or a modified form thereof) and detection of the conjugate, e.g., antigen-antibody, nucleic acid strand to complementary nucleic acid strand ("hybridization"), and protein-ligand conjugates. The conjugate is typically detected by way of a label providing a detectable signal which is attached to one or more of the binding materials. The conjugate is frequently quantitated by first determining the amount of label in the free and bound fractions, and then calculating the amount present using an algorithm and a set of standards to which the samples are compared.

The most common labels used in analyte binding assays are radioisotopes and luminescent compounds. Radioisotopes (Isotopic labeling) proffers considerably better detection in certain analyte systems than luminescent labeling. For example, the most sensitive methods for detecting nucleic acids typically involve the use of isotopic labeling, often involving radiolabelling with $^{32}P$. Luminescence is induced by energy transfer and refers to light emission that cannot be attributed merely to the temperature of the emitting body. Luminescent labels can be made to luminesce through photochemical (so-called, "photoluminescence"), chemical (so-called, "chemiluminescence") and electrochemical (so-called, "electrochemiluminescence") means. Photoluminescence, which includes fluorescence and phosphoresence, is a process whereby a material is induced to luminesce when it absorbs electromagnetic radiation such as visible, infrared or ultraviolet radiation. Chemiluminescence refers to luminescence occurring as a result of a chemical reaction without an apparent change in temperature. Electrochemiluminescence refers to luminescence occurring as a result of electrochemical processes.

In localizing particular sequences within genomic deoxyribonucleic acid ("DNA"), a transfer technique described by Southern is typically employed. DNA is digested, often using one or more restriction enzymes, and the resulting fragments are separated according to size by electrophoresis through a gel. Conventionally the DNA is then denatured in situ and transferred from the gel to a solid support, the relative positions of the DNA fragments being preserved during and after the transfer to the solid support. The DNA attached to the solid support is then hybridized to radiolabelled DNA or ribonucleic acid ("RNA"), and autoradiography is used to locate the positions of bands complementary to the probe.

For many years, immobilization and hybridization of denatured DNA was carried out almost exclusively using nitrocellulose as a solid support. As time progressed, however, it became apparent that nitrocellulose was a less than an ideal solid-phase hybridization matrix, as nucleic acids are attached to the nitrocellulose support by hydrophobic, rather than by covalent interactions, and the nucleic acids are released slowly from the matrix during hybridization and washing at high temperatures. To overcome this problem, charge-modified cellulose supports, including DBM (diazobenzyloxymethyl)-cellulose and APT-cellulose, were introduced in the early 1980's to provide improved nucleic acid binding. These matrices, however, like nitrocellulose itself, also suffer from a significant disadvantage in that they become brittle when dry and cannot survive more than one or two cycles of hybridization and washing, i.e., "reprobing."

Extensive use today is made of polyamide matrices, in particular nylon matrices, as solid support for immobilization and hybridization of nucleic acids. Various types of nylon are known to bind nucleic acids irreversibly and are far more durable than nitrocellulose. As nucleic acids can be immobilized on nylon in buffers of low ionic strength, transfer of nucleic acids from gels to a nylon matrix can be carried out electrophoretically, which may be performed if transfer of DNA by capillary action or vacuum is inefficient. Two basic types of nylon membranes are commercially available, unmodified nylon and charge-modified nylon. Charge-modified nylon is preferred for transfer and hybridization as its increased positively-charged surface has a greater capacity for binding nucleic acids (See, e.g., U.S. Pat. No. 4,473,474, the disclosure of which is herein incorporated by reference). Nylon membranes must be treated to immobilize the DNA after it has been transferred, as by way of thorough-drying, or exposure to low amounts of ultraviolet irradiation (254 nm).

While polyamide matrices have found considerable use in isotopic assay systems, such matrices have not found widespread use in fluorescent assay systems. This is likely due to the fact that fluorescent assay systems employing polyamide substrates demonstrate less than desirable sensitivity. Such reduction in sensitivity has been attributed primarily to two factors—background fluorescence produced by the nylon itself, and light scattering by solid materials in contact with the reaction media (such as substrates to which reactants are attached, or walls of the containers in which measurements are made). Polyamides, such as nylon, show light-stimulated endogenous fluorescent emissions and light reflection which can coincide with the range of UV-visible wavelengths emitted from fluorophore-tagged analytes. When light in the excitation waveband causes fluorescence of the support material, interference with detection occurs if the emission waveband of the fluorophore overlaps the same.

While isotopic assays on the whole are very sensitive, they suffer from a number of disadvantages. Primarily, use of any radioisotope automatically invokes health concerns and a host of regulatory duties with respect to waste disposal, safety, handling, reporting and licensing. While present luminescent assays proffer an alternative to isotopic labeling, the sensitivity of such assays is still not within a range desired by many in the biomedical, genetic research and drug discovery communities. Additionally, isotopic labeling cannot be used in multiplex assays, in which two or more nucleic acid probes which have been separately labeled each with their own unique colored luminescent label can be simultaneously hybridized, then simultaneously detected on an array of bound nucleic acid targets affixed to the polymeric substrate. Multiplexing saves significant cost and time when compared to the traditional steps of stripping and reprobing when performing multiple queries on a given array of targets. Multiplexing also reduces error and signal degradation that is associated with multiple reprobings.

U.S. Pat. Nos. 4,837,162 and 4,921,878 to Rothman et al., disclose a dye-modified polyamide material for use in luminescent assays which is said to both reduce the background fluorescence due to the polyamide, as well as light scattering by solid materials in contact with the reaction media. By reducing such properties, it asserted that such polyamide substrates allow improved detection of fluorescent emissions from fluorophore-tagged analytes as compared to untreated polyamide substrates. These patents disclose dyeing the polyamide material with a reactive dye, that is, a dye that contains a functional group that chemically reacts with the material being dyed (See, Column 6, Lines 54–57, of U.S. Pat. No. 4,921,878), having an absorbance spectrum selected to overlap the excitation and/or emission waveband of light generated by the polyamide substrate. It is asserted that acid-reactive dyes capable of integrally binding to the polyamide do not adversely affect the properties of the polyamide substrate. Acid-reactive dyes of the azo class are said to be particularly useful and to be readily manipulated to absorb light in the necessary waveband. Non-metallic acid reactive dyes are said to be preferred.

While the dyed-polyamides disclosed in U.S. Pat. Nos. 4,837,162 and 4,921,878 have been known for over a decade, such polyamides have not found widespread acceptance in luminescent assay systems. The failure of such substrates to dominate the market may relate to the less than desirable fluoresecence quenching that has been able to be produced following the disclosures of U.S. Pat. No. 4,837, 162. It may also relate to the difficulty in identifying dyes that are both chemically-reactive with respect to the nylon and chemically non-reactive with typical analytes of interest. It is also possible that the dyes specified in these references interfere with binding of the biomolecules with the native nylon surface, either by creating an unfavorable surface for adsorption of the biomolecule, or directly competing with nylon for adsorption. One possible outcome of this competition is the creation of a biomolecule:azo dye complex which is less stable and more easily extracted and lost from the nylon surface, thus detrimentally affecting the analysis.

The biomedical and scientific communities would eagerly use fluorescent assays, as opposed to isotopic assays, if the detection sensitivity of fluorescent assays can be enhanced without increasing the potential for undesired chemical reactions. While sensitivity can be increased if the substrate on which fluorescent assays are performed does not fluoresce upon such exposure, isolation of such substrates having widespread usefulness (with respect to numerous analytes) has so far eluded the art. There is a need, therefore, for improved substrates for use in luminescent assays which lead to greater sensitivity for detecting analytes in a sample.

SUMMARY OF THE DISCLOSURE

The present application discloses a substantially non-reflective, low or non-fluorescing (from about 250 nm to about 770 nm), substrate comprising a phase-inversion support and a plurality of opaque solids that are chemically non-reactive with the phase inversion support and of a size sufficient to be partially or completely contained within, or irreversibly bound, to the phase inversion support. Such substrate significantly improves detection in luminescent assay systems with respect to the detection of a wide-variety of analytes, and enables the use of a wide variety of fluors as labeling moieties. Further disclosed is an improved fluid filtration polyamide substrate. Such polyamide substrates comprise a polyamide support impregnated (fully or partially), coated, or surface-bound, with light absorbing opaque solids, such as pigments, fillers and extenders. Such polyamide substrates can be used as solid support matrices in bioassays or in the fabrication of objects such as reaction containers, as well as filters for removing organic and/or inorganic materials.

In one representative embodiment, there is disclosed a polyamide substrate comprising a polyamide support with opaque solids, such as a pigment, as for example, carbon particles, interspersed therein. The polyamide support may comprise nylon-66. Preferably the carbon particles are amorphous, and advantageously comprise carbon black. The carbon particles preferably compose at least about 0.002% by weight of the polyamide substrate. The carbon particles may be impregnated wholly or partially within the polyamide support or may be distributed over one or more surfaces of the polyamide support. Preferably distribution of the carbon particles is substantially uniform. And more preferably, the carbon particles are uniformly impregnated throughout the polyamide support such that they are entirely encapsulated within the support leaving the polyamide surface chemically functional, and relatively unaffected by the carbon particles. The latter has been found to provide for superior binding of nucleic acids, and their expressed products, proteins and other biomolecules.

In another representative embodiment, there is provided an optically passive polyamide substrate comprising a polyamide support and opaque solids that are chemically non-reactive with the phase inversion support and of a size sufficient to be partially or completely contained within, or irreversibly bound, to the phase inversion support, the opaque solids being in a weight ratio such that said substrate is capable of absorbing light at substantially all wave lengths from about 250 to about 770 nm, more preferably from about 300 to about 700 nm, that impinge upon it. The polyamide substrate may be microporous, and may be in the form of a membrane. In one represenatative embodiment, it is presently preferred that the polyamide substrate have a reflectance of no more than 50% of incident light at any wavelength within said range of wavelengths. It is also presently preferred that the polyamide substrate is hydrophilic and skinless.

In yet another representative embodiment, there is provided an assay in which the presence or quantity of an analyte is being detected by fluorescence at an emission waveband of light that results from the excitation of a fluorescent signal label on a polyamide support by an excitation waveband of light, the improvement comprising: providing as said polyamide support an optically passive polyamide prepared by interspersing carbon particles into a polyamide support in such a manner as to substantially quench fluorescence due to the polyamide support at the excitation waveband or emission waveband, or both.

In still another representative embodiment, there is provided a substrate comprising: a phase-inversion support; and a plurality of opaque solids that are substantially chemically non-reactive with the phase inversion support and intimately bound thereto, and/or partially/completely contained within the phase-inversion support, the substrate having substantially reduced reflectance. Methods for preparing such polyamide substrates are also disclosed.

In another representative embodiment, there is provided a substrate which provides little fluorescence from about 300 nm to about 700 nm comprising: a phase-inversion support; and a plurality of opaque solids that are substantially chemically non-reactive with the phase inversion support and intimately bound to, and/or partially/completely contained within, said phase-inversion support, the substrate having substantially reduced reflectance.

In one representative method, a substrate is prepared comprising a polyamide support impregnated with, and substantially containing therein, a plurality of opaque solids, such as carbon particles, such that substantially all of the polyamide surfaces are chemically and functionally available for binding of analyte; said method comprising the steps of: formulating a casting dope comprising a solvent, non-solvent, opaque solids and polyamide(s); mixing and blending the casting dope to cause dissolution of the polyamide and opaque solids; causing an opaque solid-filled phase inversion of the casting dope; casting and then quenching a portion of the opaque solid-filled casting dope to fabricate a phase inversion substrate; and drying the substrate.

In another representative method, a substrate is prepared comprising the acts of: formulating a dope comprising a solvent, at least one non-solvent, opaque solids and at least one phase-inversion polyamide; mixing and blending the dope to cause dissolution of the polyamide and opaque solids in the dope; and producing an opaque solids-filled phase inversion membrane from the dope.

BRIEF DESCRIPTION OF THE DRAWINGS

The above description, as well as further objects, features and advantages of the present disclosure will be more fully understood with reference to the following detailed description when taken in conjunction with the accompanying drawings, wherein.

DETAILED DESCRIPTION

The present disclosure overcomes many of the problems associated with the less than desirable solid substrates used in analyte assays employing fluorescent labeling, and provides a product useful in a number of other applications, including filtration.

There is disclosed a phase-inversion substrate impregnated (fully or partially), coated, or surface-bound (or combination of the same), with opaque solids that are non-reactive with the phase inversion support and of a size sufficient to be partially or completely within, or irreversibly bound, to the phase inversion support. In a presently preferred representative embodiment, the substrate is a membrane, which may or may not carry charge. When employed in analyte assays which are based on luminescent labeling, substrates containing such opaque solids have been found to allow significantly enhanced detection of numerous analytes under many conditions. Such substrates have been seen to produce significantly less intrinsic fluorescence and light-scattering than polyamide substrates lacking the opaque solids.

By "phase inversion support" it is meant a polymeric support that is formed by the gelation or precipitation of a polymer membrane structure from a "phase inversion dope." A "phase inversion dope" consists of a continuous phase of dissolved polymer in a good solvent, co-existing with a discrete phase of one or more non-solvent(s) dispersed within the continuous phase. The formation of the polymer membrane structure generally includes the steps of casting and quenching a thin layer of the dope under controlled conditions to affect precipitation of the polymer and transition of discrete (non-solvent phase) into a continuous interconnected pore structure. This transition from discrete phase of non-solvent (sometimes referred to as a "pore former") into a continuum of interconnected pores is generally known as "phase inversion." Such membranes are well known in the art.

Typically, a phase inversion support is formed by dissolving the polymer(s) of choice in a mixture of miscible solvent(s) and non-solvent(s), casting a support pre-form, and then placing the surface of the support pre-form in contact with a non-solvent (liquid or atmosphere) diluent miscible with the solvent(s) (thereby precipitating or gelling the porous structure).

By "opaque" it is meant displaying the property of not being pervious to visible light. By "solid" it is meant a composition of matter that is not entirely either a liquid or gas, or both. A "solid" may, or may not, have internal cavities or channels. A "solid" with an internal cavity or channel may comprise a liquid or gas within the internal cavity or channel. Solids may be formed in any variety of shapes, and have a plurality of textures as well. Roughly spherical solid particles can be advantageously used. Such a solid particle may also have internal cavities or channels (i.e. a reticulated particle); the channels providing greater surface area or light absorptive characteristics. In addition, non-spherical solids such as fibers may also be advantageously used. A fiber is generally defined as a solid particle having an aspect ratio of greater than 2 units of length per 1 unit of diameter. Fibers of considerable length may also be employed in the present disclosure, thus contributing properties unique to the combination of fiber and membrane composite (i.e. improved strength) to the resultant structures.

By "intimately bound" it is meant that one substance is bound to another substance in a manner that it is not easily dissociated from the other substance. As used in this application, "intimately bound" does not include binding, which is predominantly by means of a chemical bond between the one substance and the other substance.

A presently preferred phase inversion support comprises polyamides, organic polymers formed by the formation of amide bonds between monomers of one or more types. Particularly useful polyamides in the present disclosure are nylons. Nylons comprise aliphatic carbon chains, usually alkylene groups, between amide groups. The amide groups in nylons are very polar and can hydrogen bond with each other, and are essentially/planar due to the partial double-bond character of the C—N bond. Nylons are polymers of intermediate crystallinity, crystallinity being due to the ability of the NH group to form strong hydrogen bonds with the C=O group. Nylon typically consists of crystallites of different size and perfection. It is the amorphous content of nylons that adds a diffuse scattering halo. Nylon 66, typically synthesized by reacting adipic acid with hexamethylene diamine, is a particularly preferred nylon for the present disclosure. Nylon 66 will typically contain both fluorescent and phosphorescent species which can not be extracted by conventional extraction techniques. These species are believed to be associated with the presence of α-ketoimide structures formed by thermal oxidation of the molecular backbone of the polymer, and associated with, or originating from, aldo condensation products of cyclic enone dimer and dienone trimer of cyclopentanone; all of which are present in the polymer as manufactured (See, Allen et al., *Analysis of the Fluorescent and Phosphorescent Species in Nylon-66*, Eur. Polym. J., 21(6), pp. 517–526, 1985).

A carbon-polyamide substrate of the present application can be produced by coating the surface of, or impregnating, a polyamide support, such as a mesh, with carbon black.

The polyamide, such as nylon-66, could be produced with carbon black mixed into a dope, such dopes as described in U.S. Pat. No. 3,876,738 and/or U.S. Pat. No. 4,645,602, so as to form a carbon-black filled polyamide microporous membrane substrate.

Polyamide substrates can be formed into planar solid supports, containers, and filters. Presently preferred polyamide substrates are readily wettable by the liquids with which they are to be contacted, and are preferably hydrophilic. Presently preferred polyamide substrates are also porous. The polyamide substrate may comprise a microporous membrane. The substrate is preferably also skinless, that is, the polymer organization does not change from the exterior surface to the interior surface of the polyamide. Nylon-66 is a presently preferred polyamide, particularly in the form of a skinless, hydrophilic microporous membrane.

It has been discovered by the present inventors that the fluorescence of polyamide materials, such as nylon, can be significantly reduced by addition of opaque solids that are chemically non-reactive with the phase inversion support and of a size sufficient to be partially or completely contained within, or irreversibly bound, to the phase inversion support, e.g., carbon particles. Amorphous carbon, such as carbon black, a pigment, has been found to be a particularly useful opaque solid. By the term "carbon black" it is meant an amorphous form of carbon produced commercially by thermal or oxidative decomposition of hydrocarbons, and includes: (1) animal charcoal obtained by charring bones, meat etc.; (2) gas black obtained by incomplete combustion of natural gas; (3) lamp black, obtained by burning various fats, oils, resins, etc., under suitable conditions; (4) activated charcoal prepared from wood and vegetables.

Presented with numerous possibilities for quenching the fluorescence of polyamide materials, the present inventors have found that substantially chemically non-reactive (with respect to the polyamide) opaque solids, such as carbon particles, may be physically associated with a polyamide support to allow efficient detection of numerous analytes in photoluminescent binding assays (without interference from background fluorescence). In particular, DNA binding during Southern Blot transfer has not been seen to be adversely affected by the presence of such opaque solids such as carbon black. Enhanced detection of DNA and other nucleic acids may be evidenced when polyamide substrates are impregnated (partially or wholly), coated, or surface-bound, with such opaque solids when photoluminescence assays are used.

While any opaque solid that is non-reactive with the phase inversion support and of a size sufficient to be partially or completely contained within, or irreversibly bound to the phase inversion support which has the desired fluorescence quenching properties may be used, black solids in particular, such as carbon-black, have been advantageously employed. Carbon-black absorbs energy thereby quenching the fluorescing background produced by a nylon-66 membrane. The simple chemistry of carbon black, once incorporated into the membrane, has not been found to interfere with nucleic acid binding assays, in particular with DNA binding during Southern Blot transfer.

Alternatively, it is believed that a suitable coating of pigment (by which it is meant a solid that reflects light or certain wavelengths while absorbing light of other wavelengths, without producing appreciable luminescence) either impregnated partially or mostly within the polymer matrix or properly and intimately bound to the surfaces (internal and external surfaces of the porous matrix) of such a microporous membrane may also be employed; especially when it is desirable to have the chemical functionality of the pigment available for interaction with analytes.

The present inventors have also discovered that activated carbon-coated polyamide substrates, in particular nylon substrates, and polyamide substrates having activated carbon partially encompassed therein (i.e., having a portion of the activated carbon particles exposed on the surface of the polyamide substrate) have been found to provide enhanced removal of organic contaminants in drinking water as well as particle removal. The increase in removal of organic contaminants from fluids which is evidenced using activated carbon-polyamide substrates, as opposed to nylon alone, or activated carbon alone, may be due to the greater surface proffered when the activated carbon particles are dispersed among the polyamide support.

Figure 1:
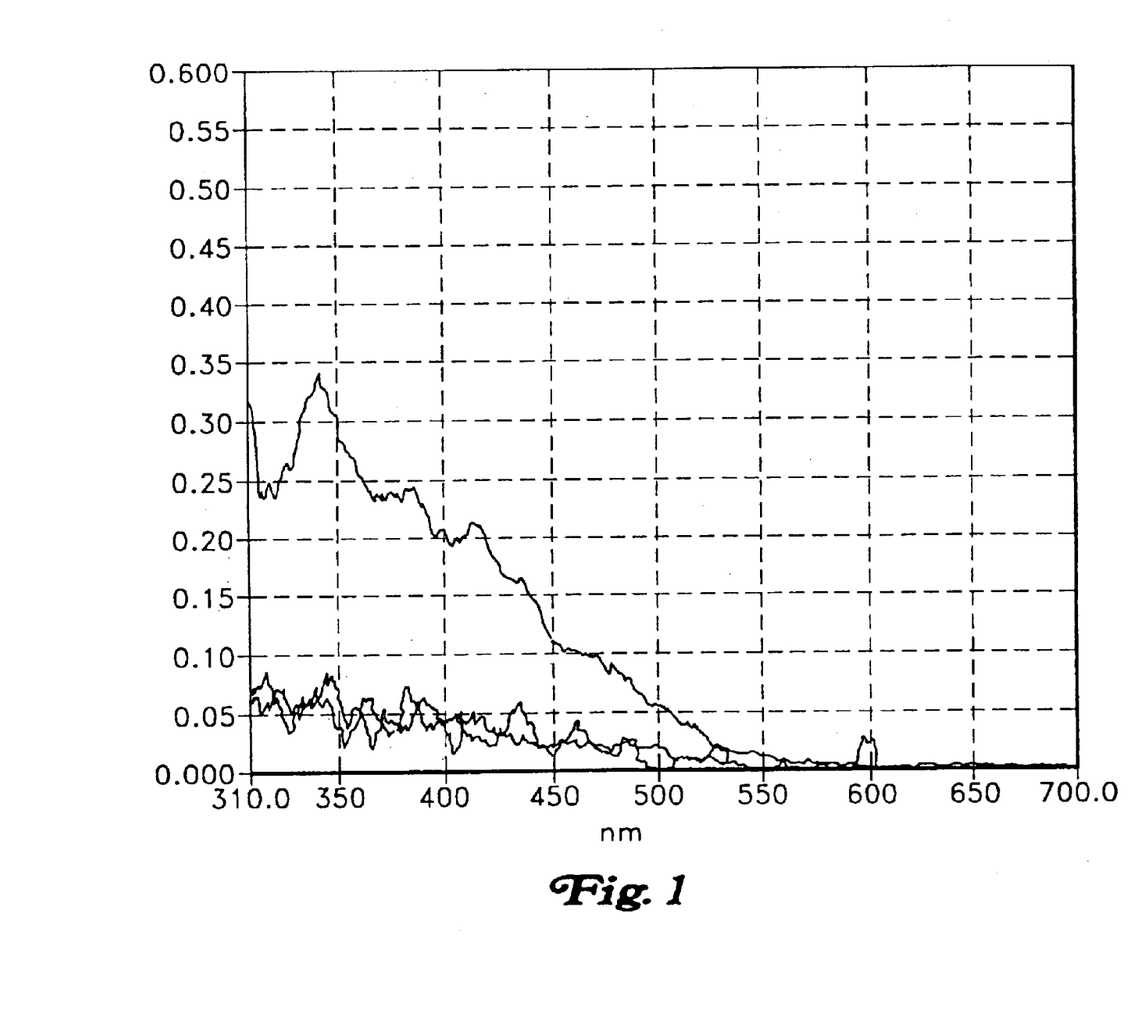
FIG. 1 is a fluorescence spectral synchronous kinetic scan, using a constant Stokes shift set at 25 nm (i.e., detector frequency centered on a wavelength which is 25 nm higher than the excitation light frequency over the wavelengths scanned), of nylon-66 (top curve), and nylon-66 impregnated with carbon black at a weight ratio (nylon-66: carbon black) of 10:1, 12:1, and 15:1 (bottom curves).

Now turning to FIG. 1, there is shown a fluorescence spectral synchronous kinetic scan, using a Stokes shift set at 25 nm, of nylon-66 (top curve), and nylon-66 impregnated with carbon black at a weight ratio (carbon black:nylon-66) of 1:10, 1:12, and 1:15 (bottom curves). As evidenced, carbon black was seen to significantly reduce the fluorescence of nylon-66. The spectral kinetic scans of the 1:10, 1:12 and 1:15 substrates were found to be within the background noise for the particular equipment employed.

Figure 2:
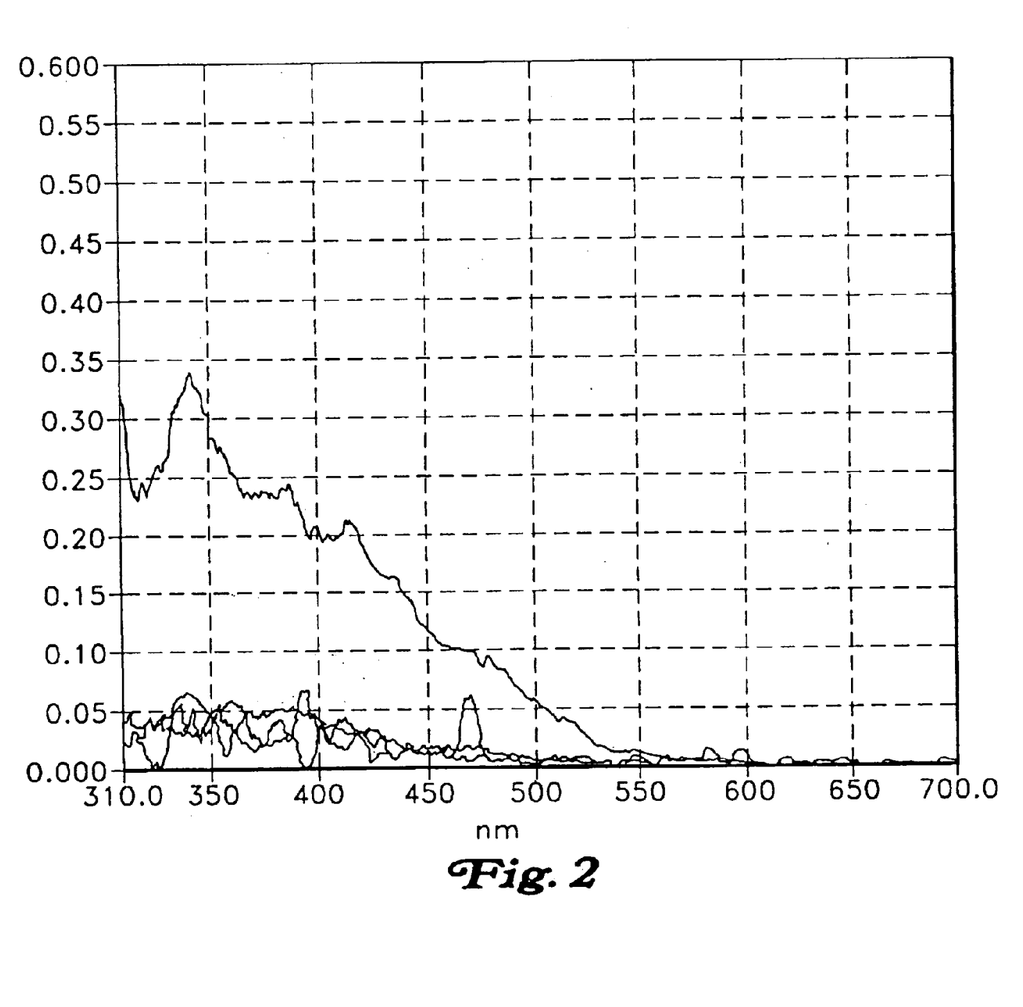
FIG. 2 is a fluorescence spectral synchronous kinetic scan, using a Stokes shift set at 25 nm, of nylon-66 (top curve), and nylon-66 impregnated with carbon black at a weight ratio (nylon-66/carbon black) of 21:1 and 31:1 (bottom curves).

Now turning to FIG. 2, there is shown a fluorescence spectral synchronous kinetic scan, using a detection stokes shift set at 25 nm, of nylon-66 (top curve), and nylon-66 impregnated with carbon black at a weight ratio (carbon black:nylon-66 ) of 1:21 and 1:31 (bottom curves). Even though carbon comprised a significantly lower percentage of the weight of the substrate as compared to the substrates of FIG. 1, carbon black was seen to reduce significantly the fluorescence of nylon-66. The spectral kinetic scan of the 1:21 and 1:31 substrates was found to be within background noise for the particular equipment employed.

Figure 4:
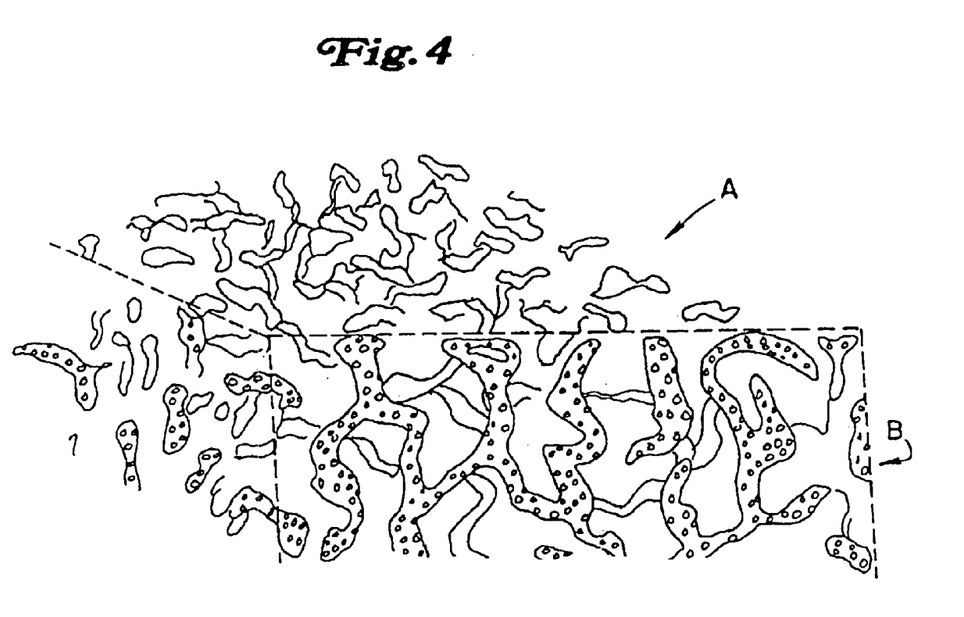
FIG. 4 is a cross-sectional drawing of a preferred opaque solid, carbon particles, dispersed within the matrix of a polyamide phase inversion microporous membrane support.

Now turning to FIG. 4, there is shown a cross-sectional drawing of a presently preferred opaque solid, carbon particles, dispersed within the matrix of a polyamide phase inversion microporous membrane support. Surface (A) illustrates the normal surface of a nylon phase inversion membrane support, while surface (B) illustrates a cross-sectional view of such membrane support showing embedded carbon particles within the solid nylon matrix.

EXAMPLE 1

A coating of fluorescent dye (fluorescein which is a yellow fluorone dye (hydroxylated xanthene)) was air dried on two nylon-66 plates, one filled with carbon black, the other having no carbon black. The coated plates were scanned on a luminescence spectrometer.

These spectra indicated that the nylon-66 plate which did not contain carbon black emitted a broader band shape, suggesting that fluorescein emitted within the same region as the nylon-66. The carbon black filled nylon-66 plate, however, indicated that the energy was lower and slightly shifted to lower wavelengths (probably due to the coating matting the reflective energy of the plate surface).

A diluted sample of fluorescein in water was also prescanned on the luminescence spectrometer. The fluorescein spectrum indicated that the emitted energy was located near the wavelength found in the spectrum of the carbon black filled nylon-66 coated fluorescein plate.

In toto, such findings show that carbon black significantly quenches the nylon-66 background emission of energy, and fluorescence.

EXAMPLE 2

A dope formulation comprising about sixteen percent (16%) by weight Nylon-66 (Monsanto® Vydyne™ 66Z), about seventy-seven percent (77%) by weight formic acid, and about seven percent (7%) by weight methanol, was produced using the methods disclosed in U.S. Pat. Nos. 3,876,738 and 4,645,602, the disclosure of each is herein incorporated in their entirety by reference. This is the standard formulation and method used to produce the (white) control membrane.

To produce the carbon black-containing membranes of the present example, the method is similar, but altered by adding the carbon black prior to the addition of Nylon to the solvent. Specific final compositions for the dopes produced in this example, expressed in % by weight for each component are shown in Table 1A.

Briefly, the altered method consisted of the following steps: liquid components formic acid and methanol were combined and allowed to react completely in a closed mixing container. After combining the formic acid and methanol, carbon black was added to the mixture prior to addition of the Nylon-66 at a weight ratio as shown in Table 1B. This was accomplished by opening the closed container and adding the required amount of carbon black directly to the liquid dope solvent mixture. Then, Nylon-66 was added to the mixture and the resulting composition was rolled in a jar mill to a maximum temperature of about thirty-four degrees Celsius (34° C.) in a constant temperature bath using a Techne C-85D constant temperature water recirculator, until all nylon was dissolved. The jar was removed from the jar mill. A cap with a sealing arrangement for a propeller shaft was fabricated to minimize volatile losses, and fitted on the jar. The dope was then mixed with a one and one quarter inch three bladed marine propeller attached to a T-line® Model # 134-1 laboratory mixer in the same vessel, in an attempt to thoroughly disperse the carbon particles. This second mixing step continued for about 1 hour at about 450 RPM.

A small portion (approximately 20 ml) of the dope was subsequently cast and quenched in a laboratory apparatus to simulate the casting process described in U.S. Pat. No. 3,876,738, to produce a single layer, non-reinforced microporous nylon membrane approximately 5 mils in thickness while wet. The membrane was subsequently washed in deionized water, folded over onto itself (to form a structure of approximately 10 mils wet) and dried under conditions of restraint to prevent shrinkage in either the machine direction (x-direction) or cross direction (y-direction). The membrane was found to be strong enough physically to withstand further processing (rinsing, drying, handling, etc), much the same as membrane without carbon added. When the membrane was rubbed vigorously, or when an adhesive tape was applied and removed, no carbon was displaced except that which was trapped in nylon pieces that were physically damaged and removed. Substantially all carbon remained intimately bound to the nylon matrix.

A small sample of dried, double-layer, non-reinforced nylon membrane having a combined thickness of about eight (8) mils after shrinkage (z-direction, after the collapsing wet pore structure was complete) was obtained on which a number of physical measurements were made, as follows:

An initial bubble point ("IBP") and foam-all-over-point ("FAOP") was measured, as described in U.S. Pat. No. 4,645,602, using deionized water as a wet fluid. Mean flow pore ("MFP") tests were undertaken as in ASTM F316-70 and ANSI/ASTM F316-70. Water flow rate measurements of the non-reinforced microporous nylon membrane were performed as described in U.S. Pat. No. 4,473,475. Dry membrane thickness was measured with a ½ inch diameter platen dial thickness indicator gauge (accuracy ±0.05 mils (=0.00005 inches)). Fluorescence of the membrane was measured on a Perkin-Elmer LS50B Luminance Spectrophotometer with excitation/emission set at 290/320 nm respectively (excitation/emission slits both set at 2.5 nm). The L (lightness) value was determined using a Macbeth Coloreye 3100 colorimeter. The L-value is part of the CIE L*a*b* standard for colorimetric analysis, one hundred (100) being pure white, and zero (0) being total black. The L-value provides a useful measurement of shades of gray.

MFP, IBP, FAOP and flow were seen to change with the addition of carbon to the formulation in a manner not directly correlatable with the increase in carbon concentration. It is believed that a direct correlation was not seen due to differences in heat build-up during mixing of the dope. It is known that the structure of the dope can be changed by temperature increases above the original formulation temperature (See, U.S. Pat. No. 6,056,529, issued May 2, 2000, the disclosure of which is hereby incorporated by reference). Fluorescence intensity, on the other hand, was correlatable to the concentration of carbon particles in the substrate. A 1:52 carbon:nylon mix substrate was found to exhibit approximately 82.84% less fluorescence than a standard white nylon membrane. A 1:15 carbon:nylon mix substrate was found to exhibit approximately 93.13% less fluorescence than a standard white nylon membrane.

TABLE 1A

| COLOR | FORMIC | METHANOL | NYLON | CARBON |
|---|---|---|---|---|
| Carbon:Nylon | | | | |
| White (0:100) % by weight | 76.94% | 7.08% | 15.98% | 0.00% |
| Gray (1:52) % by weight | 76.90% | 6.87% | 15.92% | 0.31% |
| Black (1:15) % by weight | 76.35% | 6.80% | 15.79% | 1.06% |

TABLE 1B

| COLOR (Carbon: Nylon) | MFP (micron) | IBP (psig) | FAOP (psig) | THICK- NESS (mils) | FLOW (ml/min) | WHITE- NESS (L-value) | FLUORES- ENCE (intensity) |
|---|---|---|---|---|---|---|---|
| White (0:100) | 0.434 | 43.5 | 48.0 | 7.7 | 49.1 | 98.15 | 0.75 |
| Gray (1:52) | 0.490 | 35.0 | 42.0 | 8.0 | 82.0 | 59.11 | 0.13 |
| Black (1:15) | 0.334 | 48.0 | 55.0 | 9.3 | 35.5 | 35.94 | 0.05 |

A two by four centimeter piece was subsequently removed from each of the white, black and gray membranes above. The tip of a nine-inch Pasteur pipette was heated and stretched to reduce the diameter of the tip. This was then used to spot the membranes with a solution containing 0.1 grams of 1% by weight aqueous mixture of fluorescent microspheres (fluorescein labeled uniform microspheres obtained from Bangs Laboratories, Inc., catalog # FC03F) with an approximately three-micron diameter in ten milliliters of distilled water. Under observation, the spots were about 250 microns in diameter. The samples with the fluorescent microspheres were then brought into a darkroom, and illuminated with a hand held ultraviolet light source. With regard to background intensity, the white membrane itself glowed brightly, whereas the gray membrane was much muted and just slightly visible, and the black membrane disappeared entirely. In each case, the spots placed upon the top of the membranes glowed very well.

EXAMPLE 3

Bacteriophage lambda DNA was digested with Hind III and resolved through a 1.0% agarose gel for ~2 hr in Tris-acetate EDTA buffer (40 mM Tris-acetate, 1 mM EDTA). Twenty (20) ng, 4 ng, and 0.8 ng samples of the digested lambda DNA were run in three separate lanes (demarcated at FIG. 3 as "1, 2, 3"). Three lane "sets" were then transferred to individual nylon membranes containing different amounts of carbon black (demarcated at FIG. 3 as A–H).

The gels were processed in the following way prior to transfer to the nylon membranes. The gels were soaked with agitation in 500 mL of 0.13 M HCl for 10 minutes. Gels were then transferred into 500 mL 0.5 M NaOH/1.5 M NaCl for 30 minutes. The gels were then neutralized with 0.5 M Tris-HCl/1.5 M NaCl for 30 minutes. The gels were then inverted onto sheets of Whatman®3MM® grade chromatography paper wicks that hang into a chamber containing 800 mL of standard 10x SSC. Appropriate nylon membranes were placed on the gel and a stack of 3MM® paper and paper towels were placed on top. A weight, ~500 g, was placed on top of the stack to facilitate transfer. The transfer was allowed to proceed overnight.

The next day membranes were heated at 80° C. for 60 minutes to dry them and "fix" the nucleic acid to the nylon membrane. Blots were pre-hybridized in 5x SSC with Denhardt's solution at the appropriate temperature for a minimum of 30 minutes.

Lambda digested with Hind III was radioactively labeled following the procedure outlined in the MegaPrime Kit from Amersham Pharmacia Biotech. The heat-denatured probe was then added to the blots in 5x SSC/Denhardt's solution and hybridizations were carried out overnight at the appropriate temperature.

The following morning the blots were washed in solutions of decreasing ionic strength and increasing temperature (stringency washes) to remove non-specific signal. The blots were wrapped in plastic film and exposed to X-ray film in exposure cassettes containing intensifying screens.

Figure 3:
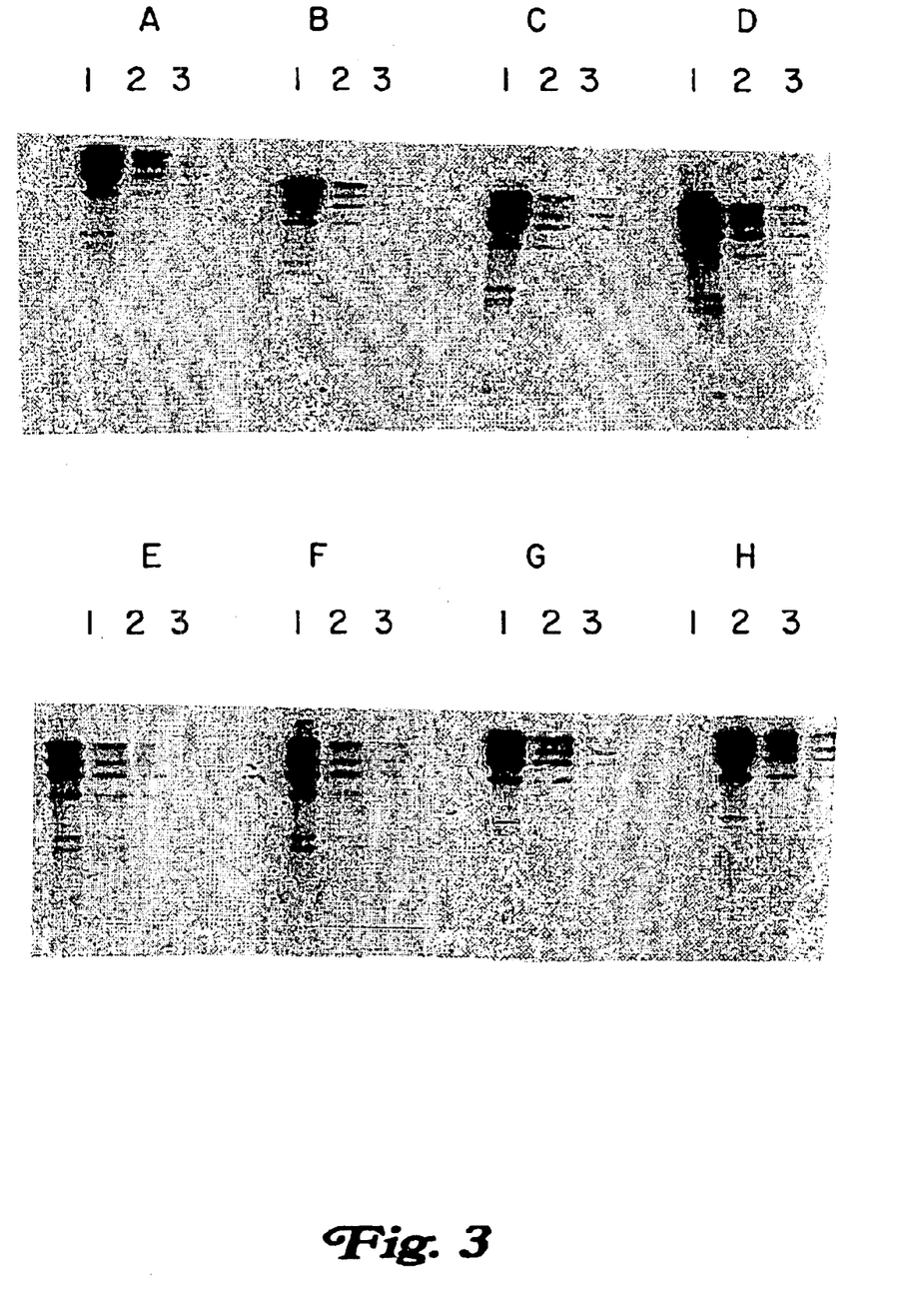
FIG. 3 is a southern blot of bacteriophage lambda DNA digested with Hind III transferred to nylon membranes having varying amounts of carbon black.

FIG. 3 illustrates the results of such experiment with respect to a nylon membrane having a carbon black:nylon ratio of (A) 1:10 (weight:weight); (B) 1:7.5 (weight:weight); (C) 0:100 (weight:weight) (i.e., control), (E) 1:7.5 (weight:weight) (i.e., repeat of (B)); (F) 1:5 (weight:weight), and (G) 0:100 (weight:weight) (i.e., control repeat). Also illustrated are the results seen on a commercially available product, (D) and (H), Amersham® Hybond N+®.

It can be seen that the carbon membrane (tested at 3 different high-level carbon black loadings) successfully binds nucleic acid when compared to a standard, unreinforced membrane, (C) and (G), composed of the same "casting dope" without added carbon black and to a commercially available nylon membrane, Amersham Inc., Hybond N+®, (D) and (H), widely utilized in Southern Blot applications.

From this data, it is also clear that the bound nucleic acid is available for hybridization with the radiolabelled probe; thus the added carbon black did not affect the accessibility of the DNA for hybridization techniques, nor the efficiency of binding of DNA to Nylon.

EXAMPLE 4

A sample of white membrane (carbon:nylon ratio=0:100), and a sample of carbon black impregnated membrane (carbon:nylon ratio=1:10), were prepared by the method described in Example 2 (the only difference being the ratio of carbon black to nylon used in the formulation). These samples were then submitted for cross sectional Scanning Electron Photomicrographs.

The particular grade of carbon black which was used in this, and all other examples set forth above, was Manufacturer Degussa-Huls, grade Printex U Channel black (control number 990225), CAS # 1333-86-4. Channel black typically has a nominal particle size from about 120 to about 200 angstroms before congealing. Congealed particles can be substantially larger. Actual particle size has not been measured. It is preferable to transfer and mix the carbon black in a manner that minimizes clumping, which will affect the uniformity of dispersion within the nylon. For this reason, the second, more vigorous, mixing step has been employed using a low shear mixing head, such as described in Example 2. Such mixing equipment is readily available in the market; for example, Lightning® mixers, or other propeller or turbine based stirring mixers. Such equipment and techniques for mixing can be readily adapted for these purposes by one skilled in the art.

Figure 5A:
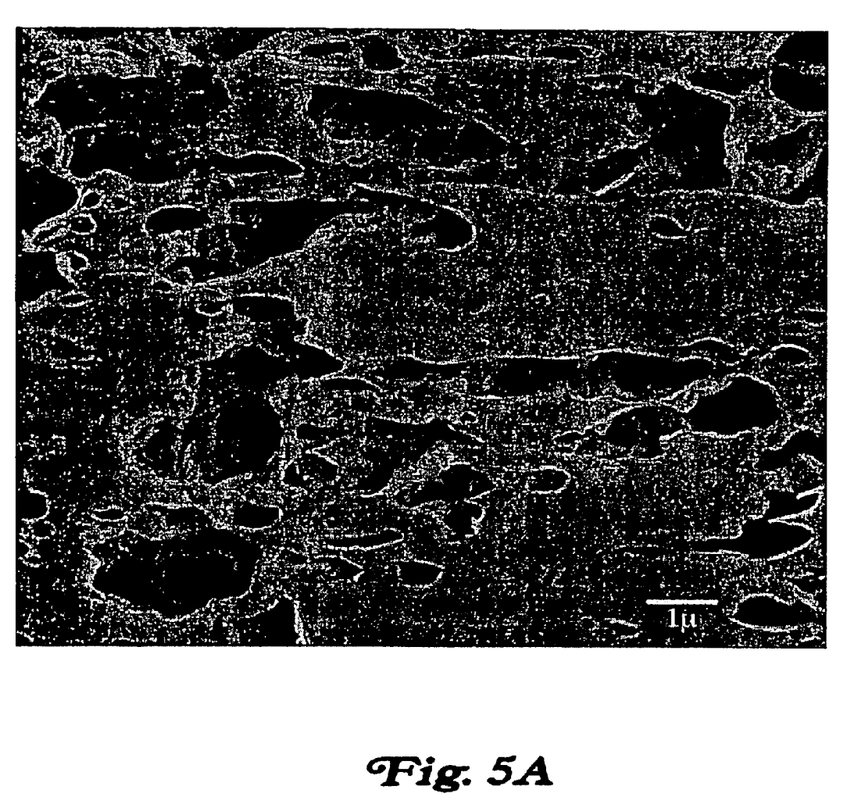
FIGS. 5a and 5b are a scanning electron micrograph of a polyamide phase inversion microporous membrane support, with and without, incorporation into its matrix of a preferred opaque solid, carbon particles.
Figure 5B:
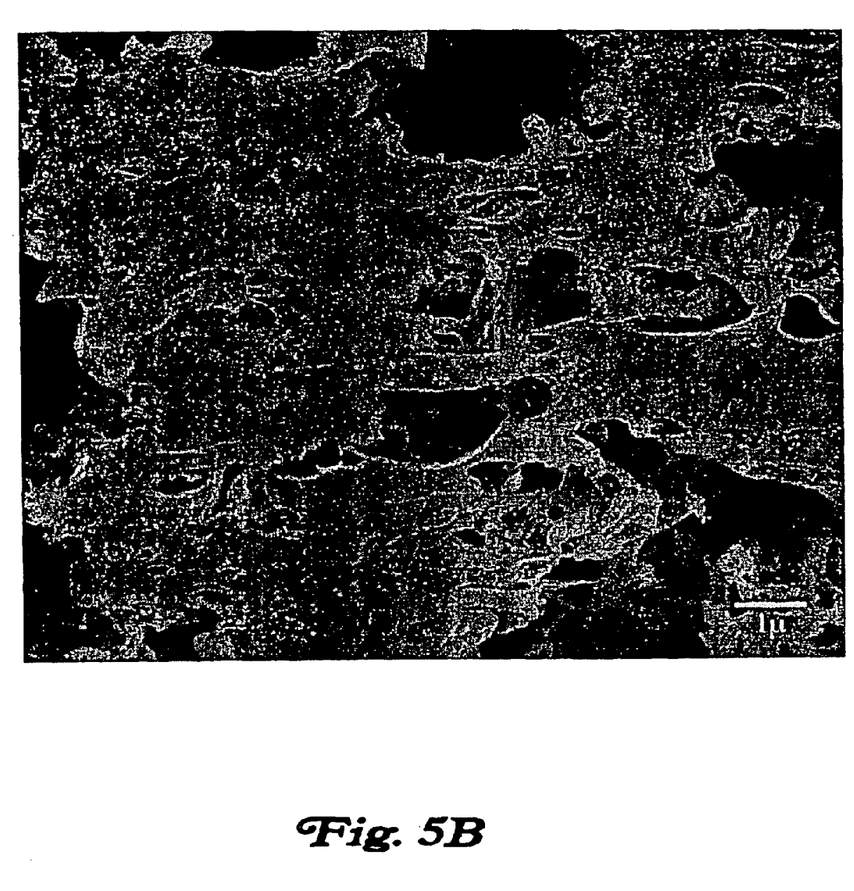

The white membrane (carbon:nylon ratio=0:100), and carbon black impregnated membrane (carbon:nylon ratio= 1:10) samples were filled with a neutral media, frozen, then cut using a microtome device in cross section, which opened up the internal structure of the nylon matrix. After thawing, the neutral media was removed and samples were prepared for SEM by normal technique. FIG. 5a shows the white membrane, containing no carbon black (magnification=10,000×). FIG. 5b shows the internal structure of the nylon, wherein the impregnated carbon black particles are readily visible as inclusions within the nylon matrix (magnification=10,000×). These SEM photos demonstrate the impregnation and substantially wholly incorporated carbon particles in the polyamine support, as illustrated in FIG. 4.

In the representative embodiment shown in FIG. 5b, substantially all of the carbon black particles are embedded within the nylon matrix, visible only through the area, which has been sliced. There are few if any visible particles at or near the (natural, uncut) internal pore surfaces that can be viewed in the FIG. 5b SEM photo. Such distribution suggests that the internal pore surfaces of the nylon are not chemically affected by the presence of the carbon black particles.

EXAMPLE 5

A dope formulation comprising about sixteen percent (16%) by weight Nylon-66 (Monsanto® Vydyne™ 66Z), about seventy-six percent (76%) by weight formic acid, and about eight percent (8%) by weight methanol, was produced using the methods disclosed in U.S. Pat. Nos. 3,876,738 and 4,645,602, the disclosure of each is herein incorporated by reference. This is the standard formulation and method used to produce the (white) control membrane.

To produce the carbon black-containing membranes of the present example, the method is similar, but altered by adding the carbon black prior to the addition of Nylon. Specific final compositions for the dopes produced in this example, expressed in % by weight of each component are shown in Table 2A.

Briefly, the altered method consisted of the following steps: liquid components formic acid and methanol were combined in a Silverson® Model # L4SRT\SU (Sealed Unit) mixer using a one liter stainless steel vessel at about 1000 rpm for 15 minutes and allowed to react in the closed container. After mixing the formic acid and methanol, carbon was added to the solution prior to addition of the Nylon-66 at a weight ratio as shown in Table2A. This was accomplished by opening the closed container and adding the required amount of carbon black directly to the formic/methanol solution. The carbon was then dispersed with the Silverson® for about 10 minutes at about 5000 rpm. This was done to completely disperse the carbon black and facilitate its uniform distribution throughout the mixture. Then, Nylon-66 was added to the mixture and the resulting composition was mixed with a three inch diameter three-blade propeller mounted on a T-line® Model # 134-1 laboratory mixer in the same vessel. A cap with a sealing arrangement for the propeller shaft was fabricated to minimize volatile losses. The vessel and mixer arrangement was then placed over a constant temperature bath such that the majority of the vessel was submerged in the bath, with bath temperature controlled at 34° C. The prop mixer speed was set initially at about 350 rpm for one-half hour; it was then slowed to about 70 rpm for another 3 hours to completely dissolve the nylon into solution. After the three hour mixing, the speed of the mixer was again increased to about 350 rpm for about one-half hour to completely homogenize the dope.

A small portion (approximately 20 ml) of the dope was subsequently cast and quenched in a laboratory apparatus to simulate the casting process described in U.S. Pat. No. 3,876,738, to produce a single layer, non-reinforced microporous nylon membrane approximately 5 mils in thickness while wet. The membrane was subsequently washed in deionized water, folded over onto itself (to form a structure of approximately 10 mils wet) and dried under conditions of restraint to prevent shrinkage in either the machine direction (x-direction) or cross direction (y-direction). The membrane was found to be strong enough physically to withstand further processing (rinsing, drying, handling, etc), much the same as membrane without carbon added. When the membrane was rubbed vigorously, or when an adhesive tape was applied and removed, no carbon was displaced except that which was trapped in nylon pieces that were physically damaged and removed. Substantially all carbon remained intimately bound to the nylon matrix. By visual (macro) inspection for color uniformity across the sheet, and microscopic inspection for evidence of clumping, it appeared that the carbon dispersion of the present example was more uniform than in Example 2. This is presently believed to be a result of the high-shear dispersion mixing of carbon particles in the solvent prior to the addition of the Nylon.

A small sample of dried, double-layer, non-reinforced nylon membrane having a combined thickness of about eight (8) mils after shrinkage (z-direction shrinkage, after the wet pore structure collapse upon drying was complete) was obtained on which a number of physical measurements were made, as follows:

An initial bubble point ("IBP") and foam-all-over-point ("FAOP") were measured, as described in U.S. Pat. No. 4,645,602, using deionized water as a wet fluid. Dry double layer membrane thickness was measured with a ½ inch diameter platen dial thickness indicator gauge (accuracy±0.05 mils=0.00005 inches). The L (lightness) value was determined using a Macbeth Coloreye 3100 colorimeter. The L-value is part of the CIE L*a*b* measurement for calorimetric analysis, one hundred (100) being pure white, and zero (0) being total black. The L-value provides a useful measurement of shades of gray.

TABLE 2A

| COLOR | (Formulations) | | | |
| --- | --- | --- | --- | --- |
|  | FORMIC | METHANOL | NYLON | CARBON |
| Carbon:Nylon |  |  |  |  |
| White (0:100) % by weight | 76.14% | 7.95% | 15.91% | 0.00% |
| Gray (1:83) % by weight | 75.87% | 8.09% | 15.85% | 0.19% |

TABLE 2A-continued

| COLOR | (Formulations) | | | |
|---|---|---|---|---|
| | FORMIC | METHANOL | NYLON | CARBON |
| Black (1:15) % by weight | 75.13% | 8.18% | 15.69% | 1.00% |

TABLE 2B

| | Carbon/Nylon Content | IBP (psig) | FAOP (psig) | Thickness double layer (mils) | Whiteness L value |
|---|---|---|---|---|---|
| White | 0:100 | 67 | 77 | 8 | 98 |
| Gray | 1:83 | 70 | 80 | 8 | 63 |
| Black | 1:15 | 61 | 65 | 9 | 39 |

The descriptive use of the color "Gray" in Tables 2A and 2B is only to suggest that the specific color developed in this example appears to the human eye to be gray in comparison to white and black. Clearly, the use of the terms "white" and "black" are similarly flawed. A more precise measurement is the "L" value, which has been previously described, and is a value on a continuous, unitless comparison scale.

It is expected that, with routine experimentation, the full range of white to gray to black colors at a full range of useful pore sizes, thickness, etc., may be realized by manipulation of formulae, mixing conditions, and casting conditions familiar to those skilled in the art. Such formulae and mixing conditions will need to be optimized to ensure robustness, uniformity, and reproducibility of the product. We have demonstrated here that with simple manipulations of formulae and the use of proper dispersion mixing that it is possible to produce and characterize such products.

It is expected that, with routine experimentation, optimal results for high sensitivity and low background fluorescent noise can be obtained by simple manipulation of the variables already disclosed, e.g., pore size, total opaque solids, thickness, etc., and/or other variables in membrane production which are familiar to those skilled in the art of membrane science.

While the disclosure has been described with respect to preferred embodiments, those skilled in the art will readily appreciate that various changes and/or modifications can be made to the disclosure without departing from the spirit or scope of the disclosure as defined by the appended claims. All references cited in this specification are herein incorporated by reference to the same extent as if each individual reference was specifically and individually indicated to be incorporated by reference.

What is claimed is:

1. A substantially non-reflective substrate which provides little fluorescence from about 300 nm to about 700 nm comprising:
    a phase-inversion support; and
    a plurality of opaque solids that are substantially chemically non-reactive with the phase inversion support and intimately bound to, and/or partially/completely contained within, said phase-inversion support.

2. A substrate of claim 1 wherein the phase-inversion support comprises polyamides.

3. A substrate of claim 1 wherein the opaque solids are pigments.

4. A substrate of claim 1 wherein the opaque solids are carbon particles.

5. A substrate of claim 1 wherein the phase inversion support has been charge-modified.

6. A substrate of claim 4 wherein carbon particles are less than five microns in size.

7. A substrate of claim 4 wherein the carbon particles are substantially uniformly distributed throughout the polyamide support.

8. A substrate of claim 4 wherein the carbon particles are partially incorporated into the polyamide support.

9. A substrate of claim 4 wherein the carbon particles are substantially wholly incorporated into the polyamide support.

10. A substrate of claim 4 wherein the polyamide has been charge-modified.

11. An optically-passive substrate comprising a phase-inversion support and opaque solids that are substantially non-reactive chemically with the phase inversion support, in a weight ratio with said phase-inversion support such that said optically-passive substrate absorbs light at substantially all wave lengths from about 300 nm to about 700 nm.

12. An optically-passive substrate as recited in claim 11 wherein the phase-inversion support comprises polyamide.

13. An optically-passive substrate as recited in claim 12 wherein the phase-inversion support is in the form of a membrane.

14. An optically-passive substrate as recited in claim 12 wherein the opaque solids are carbon particles.

15. An optically-passive substrate as recited in claim 14 wherein carbon particles are less than about 5 microns in size.

16. A substrate of claim 14 wherein the carbon particles are substantially uniformly distributed throughout the polyamide support.

17. A substrate of claim 14 wherein the carbon particles are partially incorporated into the polyamide support.

18. A substrate of claim 14 wherein the carbon particles are substantially wholly incorporated into the polyamide support.

19. A substrate of claim 14 wherein the polyamide has been charge-modified.

20. A substrate as recited in claim 18 wherein the substrate absorbs light at substantially all wavelengths from about 300 to about 700 nm.

21. A substrate as recited in claim 20 wherein the substrate has a reflectance of no more than 50% of incident light at any wavelength within said range of wavelengths.

22. A substrate as recited in claim 11 wherein the phase-inversion support is hydrophilic.

23. A substrate as recited in claim 22 wherein the phase-inversion support is skinless.

24. A substrate as recited in claim 23 wherein the phase-inversion support comprises nylon.

25. A substrate as recited in claim 24 wherein the phase-inversion support is charge-modified.

26. A substrate comprising:
    a phase-inversion support; and
    a plurality of opaque solids that are substantially chemically non-reactive with the phase inversion support and intimately bound thereto, and/or partially/completely contained within the phase-inversion support, the substrate having substantially reduced reflectance.

27. The substrate of claim 26 wherein the phase-inversion support comprises polyamides.

28. The substrate of claim 26 wherein the opaque solids are pigments.

29. The substrate of claim 26 wherein the opaque solids are carbon particles.

30. The substrate of claim 26 wherein the phase inversion support has been charge-modified.

31. The substrate of claim 29 wherein carbon particles are less than five microns in size.

32. The substrate of claim 29 wherein the carbon particles are substantially uniformly distributed throughout the polyamide support.

33. The substrate of claim 29 wherein the carbon particles are at least partially incorporated into the polyamide support.

34. The substrate of claim 29 wherein the carbon particles are substantially wholly incorporated into the polyamide support.

35. The substrate of claim 29 wherein the polyamide has been charge-modified.

36. The substrate of claim 26 wherein the phase-inversion support is in the form of a membrane.

37. The substrate of claim 26 wherein the reflectance is substantially reduced from about 300 nm to about 700 nm.

38. The substrate of claim 35 wherein the substrate has a reflectance of no more than 50% of incident light at any wavelength within the range of wavelengths.

39. The substrate of claim 26 wherein the phase-inversion support is hydrophilic.

40. The substrate of claim 39 wherein the phase-inversion support is skinless.

41. The substrate of claim 40 wherein the phase-inversion support comprises nylon.

42. The substrate of claim 26 wherein the phase-inversion support is charge-modified.

43. A substrate which provides little fluorescence from about 300 nm to about 700 nm comprising:

a phase-inversion support; and a plurality of opaque solids that are substantially chemically non-reactive with the phase inversion support and intimately bound to, and/or partially/completely contained within, said phase-inversion support, the substrate having substantially reduced reflectance.

44. The substrate of claim 43 wherein the opaque solids are fibers.

* * * * *